(12) United States Patent
Francischelli et al.

(10) Patent No.: US 6,648,883 B2
(45) Date of Patent: Nov. 18, 2003

(54) ABLATION SYSTEM AND METHOD OF USE

(75) Inventors: David E. Francischelli, Anoka, MN (US); Mark T. Stewart, Lino Lakes, MN (US); James R. Skarda, Lake Elmo, MN (US); Rahul Mehra, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/132,379

(22) Filed: Apr. 24, 2002

(65) Prior Publication Data

US 2003/0004507 A1 Jan. 2, 2003

Related U.S. Application Data

(60) Provisional application No. 60/287,202, filed on Apr. 26, 2001.

(51) Int. Cl.$^7$ ................................................ A61B 18/18
(52) U.S. Cl. ............................. 606/41; 606/27; 128/898
(58) Field of Search ............................. 606/41, 32–34, 606/48–52

(56) References Cited

U.S. PATENT DOCUMENTS

| | | | |
|---|---|---|---|
| 5,233,515 A | 8/1993 | Cosman | 364/413.02 |
| 5,540,681 A | 7/1996 | Strul et al. | 606/34 |
| 5,540,684 A | 7/1996 | Hassler, Jr. | 606/40 |
| 5,558,671 A | 9/1996 | Yates | 606/38 |
| 5,562,721 A | 10/1996 | Marchlinski et al. | 607/99 |
| 5,690,611 A | 11/1997 | Swartz et al. | 604/53 |
| 5,713,896 A | * 2/1998 | Nardella | 606/50 |
| 5,733,280 A | 3/1998 | Avitall | 606/23 |
| 5,897,533 A | 4/1999 | Glickman | 606/256 |
| 5,897,552 A | 4/1999 | Edwards et al. | 606/31 |
| 5,913,856 A | * 6/1999 | Chia et al. | 606/41 |
| 5,916,213 A | 6/1999 | Haissaguerre et al. | 606/41 |
| 5,957,961 A | 9/1999 | Maguire et al. | 607/99 |
| 5,971,980 A | * 10/1999 | Sherman | 606/34 |
| 6,080,149 A | * 6/2000 | Huang et al. | 606/32 |
| 6,096,037 A | 8/2000 | Mulier et al. | 606/49 |
| 6,112,123 A | * 8/2000 | Kelleher et al. | 607/98 |
| 6,179,834 B1 | * 1/2001 | Buysse et al. | 606/41 |
| 6,183,468 B1 | 2/2001 | Swanson et al. | 606/40 |
| 6,409,722 B1 | * 6/2002 | Hoey et al. | 606/34 |

* cited by examiner

Primary Examiner—Roy D. Gibson
Assistant Examiner—Peter Vrettakos
(74) Attorney, Agent, or Firm—Thomas G. Barry; Daniel M. Lathan (57) ABSTRACT

A system and method for creating lesions and assessing their completeness or transmurality. Assessment of transmurality of a lesion is accomplished by monitoring the impedance of the tissue to be ablated. Rather than attempting to detect a desired drop or a desired increase impedance, completeness of a lesion is detected in response to the measured impedance remaining at a stable level for a desired period of time, referred to as an impedance plateau. The mechanism for determining transmurality of lesions adjacent individual electrodes or pairs may be used to deactivate individual electrodes or electrode pairs, when the lesions in tissue adjacent these individual electrodes or electrode pairs are complete, to create an essentially uniform lesion along the line of electrodes or electrode pairs, regardless of differences in tissue thickness adjacent the individual electrodes or electrode pairs.

14 Claims, 9 Drawing Sheets

ABLATION SYSTEM AND METHOD OF USE

RELATED U.S. APPLICATION DATA

This application claims priority to Provisional U.S. Patent Application No. 60/287,202, filed Apr. 26, 2001 by Francischelli et al., incorporated herein by reference in its entirety.

BACKGROUND OF THE INVENTION

The present invention relates to tissue ablation devices generally and relates more particularly to devices adapted to ablate lines of tissue, for example for use in conjunction with an electrosurgical version of the Maze procedure.

The Maze procedure is a surgical intervention for patients with chronic atrial fibrillation (AF) that is resistant to other medical treatments. The operation employs incisions in the right and left atria which divide the atria into electrically isolated portions which in turn results in an orderly passage of the depolarization wave front from the sino-atrial node (SA Node) to the atrial-ventricular node (AV Node) while preventing reentrant wave front propagation. Although successful in treating AF, the surgical Maze procedure is quite complex and is currently performed by a limited number of highly skilled cardiac surgeons in conjunction with other open-heart procedures. As a result of the complexities of the surgical procedure, there has been an increased level of interest in procedures employing electrosurgical devices or other types of ablation devices, e.g. thermal ablation, microwave ablation, cryo-ablation or the like to ablate tissue along pathways approximating the incisions of the Maze procedure. Electrosurgical systems for performing such procedures are described in U.S. Pat. No 5,916,213, issued to Hiassaguerre, et al. U.S. Pat. No. 5,957,961, issued to Maguire, et al. and U.S. Pat. No. 5,690,661, all incorporated herein by reference in their entireties. Cryo-ablation systems for performing such procedures are described in U.S. Pat. No. 5,733,280 issued to Avitall, also incorporated herein by reference in its entirety.

In conjunction with the use of electrosurgical ablation devices, various control mechanisms have been developed to control delivery of ablation energy to achieve the desired result of ablation, i.e. killing of cells at the ablation site while leaving the basic structure of the organ to be ablated intact. Such control systems include measurement of temperature and impedance at or adjacent to the ablation site, as are disclosed in U.S. Pat. No. 5,540,681, issued to Struhl, et al., incorporated herein by reference in its entirety.

Additionally, there has been substantial work done toward assuring that the ablation procedure is complete, i.e. that the ablation extends through the thickness of the tissue to be ablated, before terminating application of ablation energy. This desired result is some times referred to as a "transmural" ablation. For example, detection of a desired drop in electrical impedance at the electrode site as an indicator of transmurality is disclosed in U.S. Pat. No. 5,562,721 issued to Marchlinski et al, incorporated herein by reference in its entirety. Alternatively, detection of an impedance rise or an impedance rise following an impedance fall are disclosed in U.S. Pat. No. 5,558,671 issued to Yates and U.S. Pat. No. 5,540,684 issued to Hassler, respectively, also incorporated herein by reference in their entireties.

Three basic approaches have been employed to create elongated lesions using electrosurgical devices. The first approach is simply to create a series of short lesions using a contact electrode, moving it along the surface of the organ wall to be ablated to create a linear lesion. This can be accomplished either by making a series of lesions, moving the electrode between lesions or by dragging the electrode along the surface of the organ to be ablated and continuously applying ablation energy, as described in U.S. Pat. No. 5,897,533 issued to Mulier, et al., incorporated herein by reference in its entirety. The second basic approach to creation of elongated lesions is simply to employ an elongated electrode, and to place the elongated electrode along the desired line of lesion along the tissue. This approach is described in U.S. Pat. No. 5,916,213, cited above and. The third basic approach to creation of elongated lesions is to provide a series of electrodes and arrange the series of electrodes along the desired line of lesion. The electrodes may be activated individually or in sequence, as disclosed in U.S. Pat. No. 5,957,961, also cited above. In the case of multi-electrode devices, individual feedback regulation of ablated energy applied via the electrodes may also be employed. The present invention is believed useful in conjunction with all three approaches

SUMMARY OF THE INVENTION

The present invention is directed toward an improved system for creating lesions and assessing their completeness or transmurality. In particular, the preferred embodiments of the invention are directed toward an improved system for creating elongated lines of lesion and assessing their completeness or transmurality. In the preferred embodiment as disclosed, the apparatus for producing the lesions is an electrosurgical device, in particular a saline-irrigated bipolar electrosurgical forceps. However, the mechanism for assessing lesion transmurality provided by the present invention is believed useful in other contexts, including unipolar R-F ablation and R-F ablation using catheters or hand-held probes. The mechanism for assessing transmurality may also be of value in the context of other types of ablation systems, particularly those which ablation occurs in conjunction with an induced rise in tissue temperature such as those applying ablation energy in the form of microwave radiation, light (laser ablation) or heat (thermal ablation).

According to the present invention, assessment of transmurality of a lesion is accomplished by monitoring the impedance of the tissue to be ablated. The inventors have determined that, particularly in the case of a saline-irrigated electrosurgical ablation device, tissue impedance first falls and then reaches a stable plateau, during which portion the lesion is completed. Thereafter, the impedance rises. Rather than attempting to detect a desired drop or a desired increase impedance as described in the above cited Yates, Hassler and Marchlinski patents, the present invention detects completeness of a lesion in response to the measured impedance remaining at a stable level for a desired period of time, hereafter referred to as an impedance plateau. In the context of R-F ablation, measurement of impedance may be done using the ablation electrodes or may be done using dedicated electrodes adjacent to the ablation electrodes. In the context of the other types of ablation discussed above, impedance measurement would typically be accomplished by means of a dedicated set of impedance measurement electrodes.

In the context of R-F ablation, the invention is believed most valuable in the conjunction with an ablation device having multiple, individually activatable electrodes or electrode pairs to be arranged along a desired line of lesion. In this context, the mechanism for determining transmurality of lesions adjacent individual electrodes or pairs may be used to deactivate individual electrodes or electrode pairs, when the lesions in tissue adjacent these individual electrodes or electrode pairs are complete. This allows the creation of an essentially uniform lesion along the line of electrodes or electrode pairs, regardless of differences in tissue thickness adjacent the individual electrodes or electrode pairs. However, the invention is also believed useful in conjunction with assessment of transmurality of lesions produced by devices having only a single electrode or single electrode pair. Similar considerations apply to the use of the present invention in the contexts of other types of ablation as listed above.

DETAILED DESCRIPTION PREFERRED EMBODIMENTS

Figure 1:
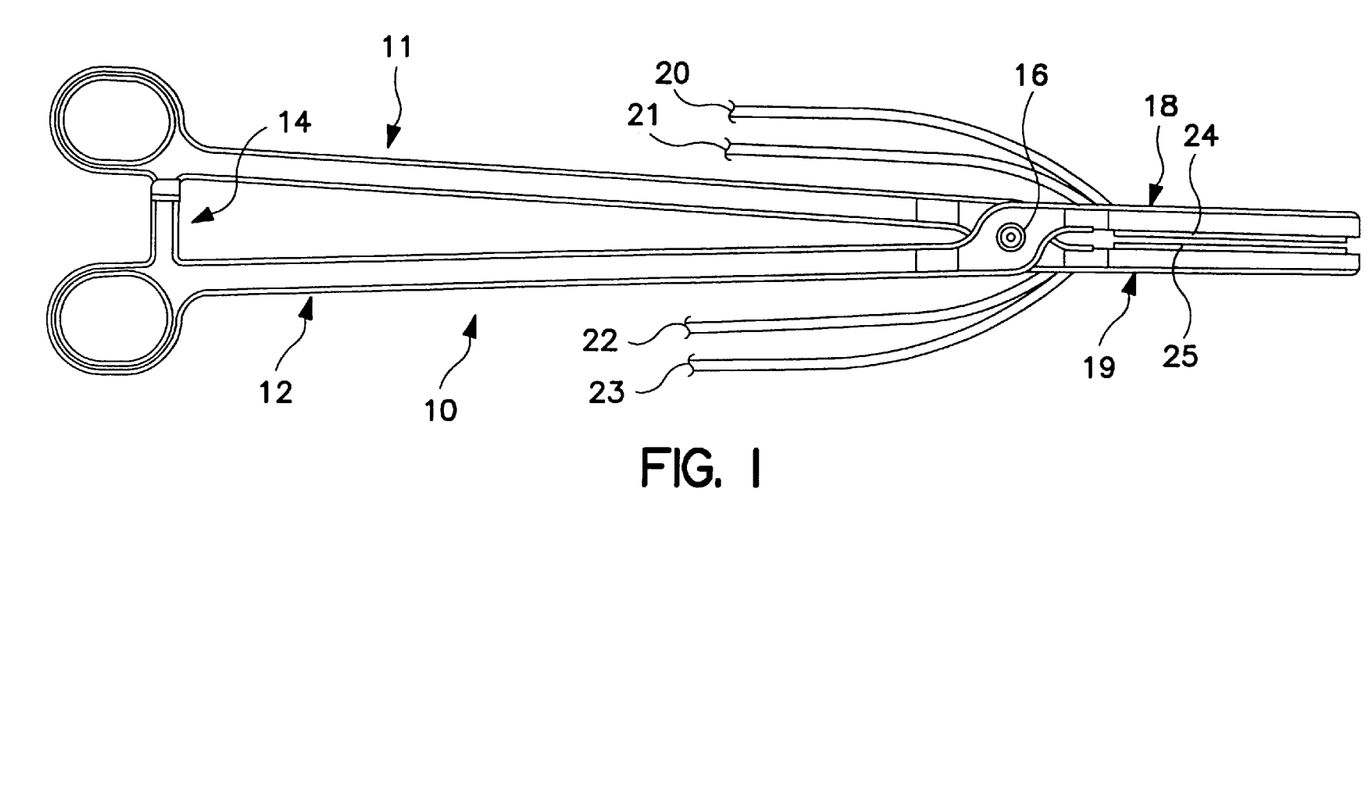
FIG. 1 is a plan view of a type of electrosurgical hemostat that may be used in conjunction with the present invention.

FIG. 1 is a plan view of a bipolar, saline irrigated electrosurgical hemostat of a type that may be employed in conjunction with the present invention. The hemostat is provided with elongated handles 11 and 12 and a lock mechanism 14, similar to a conventional surgical hemostat. The handles are connected to one another by pivot or hinge 16, and continue distally in the form of elongated jaws 18 and 19. Jaws 18 and 19 carry an elongated electrode or series of electrodes 24, 25, respectively, to which ablation energy, e.g. RF energy is applied by means of conductors 21 and 22. The electrodes are adapted to be irrigated by a saline solution or other conductive fluid along their length, provided via inlet tubes 20 and 23. In operation, tissue to be ablated is compressed between the jaws, and RF energy is applied between the electrode or electrode sets 24 and 25, as generally described in U.S. Pat. No. : 6,096,037 issued to Mulier et al incorporated herein by reference in its entirety.

Figure 2A:
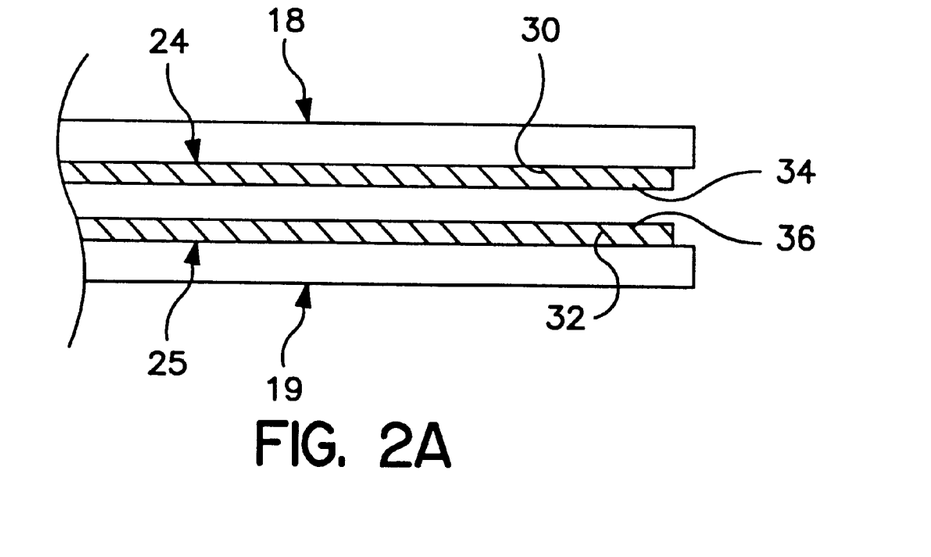
FIGS. 2a and 2b illustrate alternative electrode configurations for a hemostat generally according to FIG. 1.

FIG. 2a shows a first embodiment of an electrode arrangement for a hemostat generally as illustrated in FIG. 1. Illustrated components correspond to identically numbered components in FIG. 1. In this embodiment, electrodes 24 and 25 take the form of elongated coil electrodes 30 and 32, mounted around porous tubes 34 and 36, through which saline or other conductive fluid is delivered. The arrangement of the electrodes may also be reversed, for example placing coils 30 and 32 within elongated porous tubes 34 and 36, to accomplish a similar result. Alternatively, any other arrangement for providing an elongated electrode and delivery of saline solution along the length thereof may be substituted. The particular configuration of the electrode is not critical to the present invention. For example, irrigated electrodes corresponding to those described in U.S. Pat. No. 6,096,037 issued to Mulier, et al., U.S. Pat. No. 5,876,398 issued to Mulier, et al., U.S. Pat. No. 6,017,378 issued to Brucker, et al or U.S. Pat. No. 5,913,856 issued to Chia, et al., all incorporated herein by reference in their entireties may also be substituted. It should also be noted that while the electrode system as illustrated in FIG. 2a is a bipolar system, the invention may also be employed in conjunction with unipolar electrodes and/or in the form of a probe or a catheter. In some embodiments, irrigation of the electrodes may be omitted.

Figure 2B:
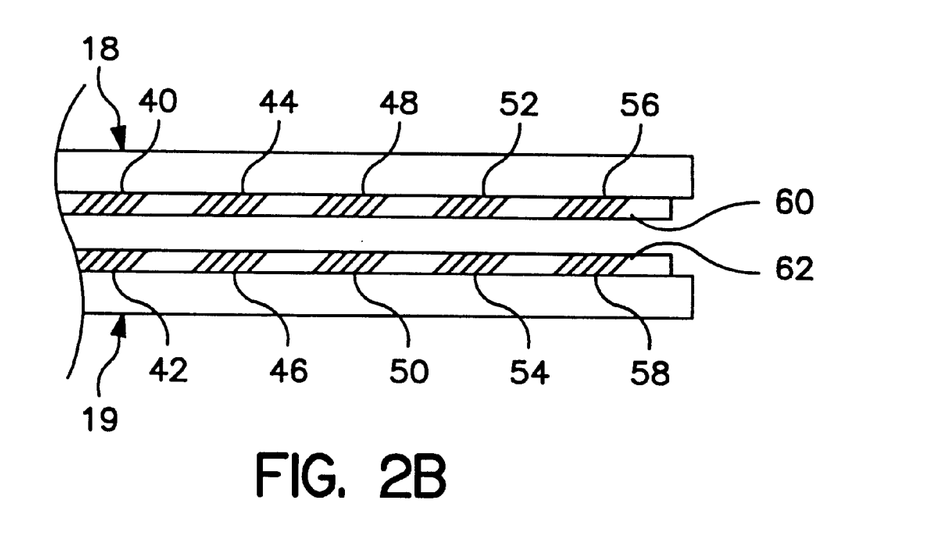

FIG. 2b illustrates an alternative embodiment of an electrode system for a hemostat generally as illustrated in FIG. 1. In this case, rather than a single pair of electrodes, multiple electrode pairs are provided. The electrode pairs comprise coil electrodes 40 and 42, 44 and 46, 48 and 50, 52 and 54, and 56 and 58. However, other pairings of electrodes might also be substituted, for example, pairing electrodes 40 and 44, electrodes 48 and 52 or the like. In this embodiment, the electrode pairs are mounted around porous plastic tubes 60 and 62 through which saline or other electrically conductive fluid is delivered. As in the case with the embodiment of FIG. 2a, the arrangement of these electrodes may readily be reversed, placing the electrodes within the lumen of plastic tube 60 or 62 and any other arrangement providing multiple, irrigated electrodes may also be substituted. As in the case of the embodiment of FIG. 2a, unipolar electrodes might be substituted for the multiple bipolar pairs as illustrated and/or the invention may be practiced in conjunction with a multi-electrode probe or catheter. While the particular arrangement of electrodes is not believed critical to practicing the present invention, it is believed that the invention may be most beneficially practiced in conjunction with a set of linearly arranged bipolar electrode pairs as illustrated in FIG. 2b.

In use, the hemostat is arranged so that the tissue to be ablated is located between the jaws 18 and 19, and pressure is applied in order to compress the tissue slightly between the jaws to ensure good electrical contact. All electrode pairs may be activated individually and may be individually deactivated when the lesions between the individual electrode pairs are completely transmural. Alternatively, electrode pairs could be activated sequentially, with one pair deactivated upon a detection of a complete lesion between the electrode pair, followed by activation of the next sequential electrode pair. Corresponding use of the invention in conjunction with a series of unipolar electrodes, for example corresponding to electrodes along one of the two jaws in conjunction with a remote ground plate or a similar series of individually activatable electrodes on a catheter or probe in conjunction with a ground plate is also possible.

Figure 3:
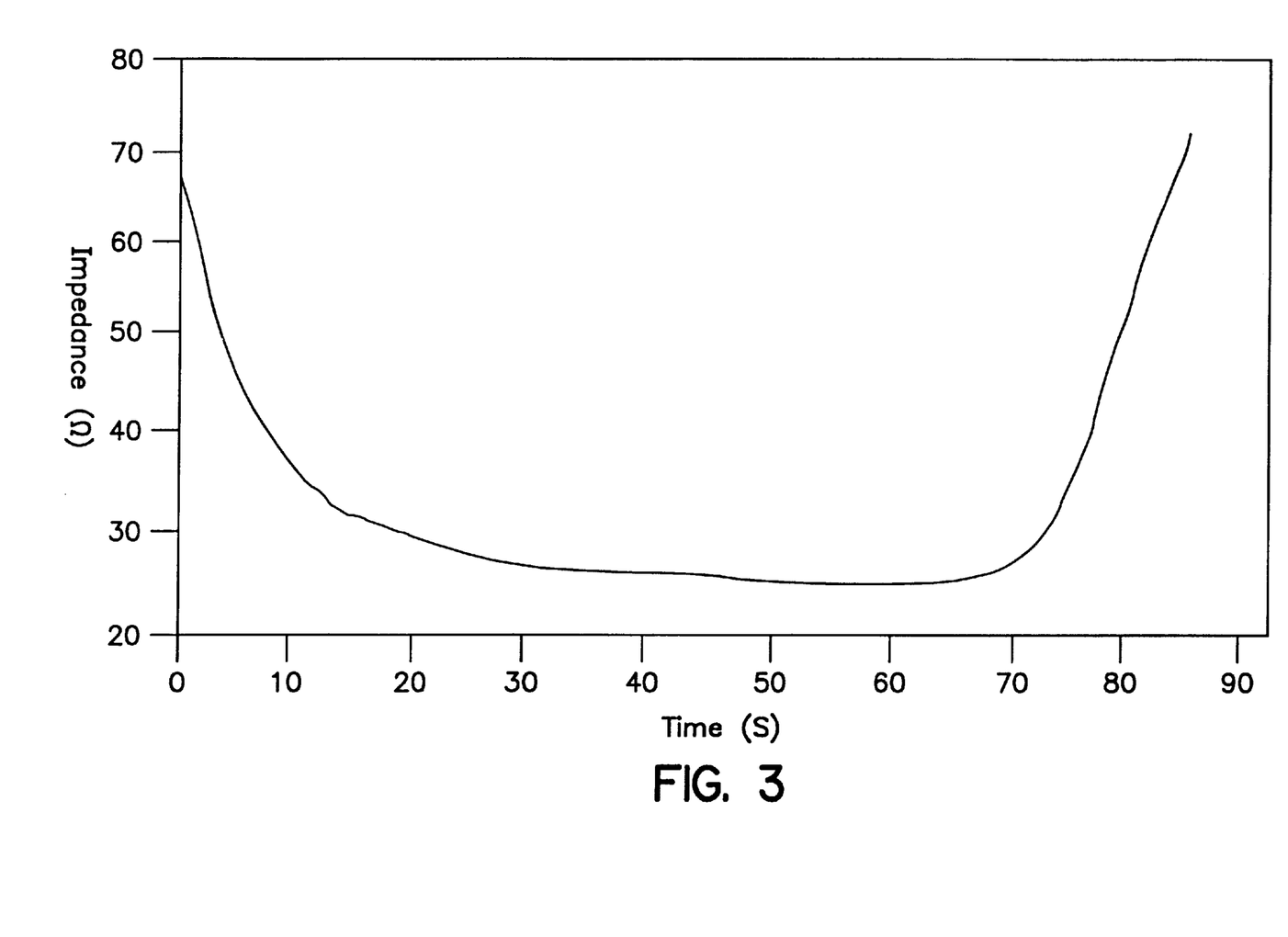
FIG. 3 illustrates the fall and plateau of impedance measured across tissue ablated using a bi-polar, saline irrigated electro surgical hemostat.

FIG. 3 is a graph illustrating measured impedance versus time across tissue located between the electrodes of an irrigated bipolar hemostat as illustrated in FIG. 1. FIG. 3 illustrates the drop in impedance followed by an impedance plateau, ultimately followed by an impedance rise. The impedance plateau is the primary indicator of transmurality employed by the present invention. Following the impedance plateau, as tissue is desiccated or as steam forms in the tissue, an impedance rise will generally occur. In some embodiments of the invention, the detection of this rise in impedance is employed as an alternative or mechanism for assessing transmurality and/or as a safety mechanism in order to assure shut off of the ablation electrodes before excessive physical damage to the tissue results.

Figure 4:
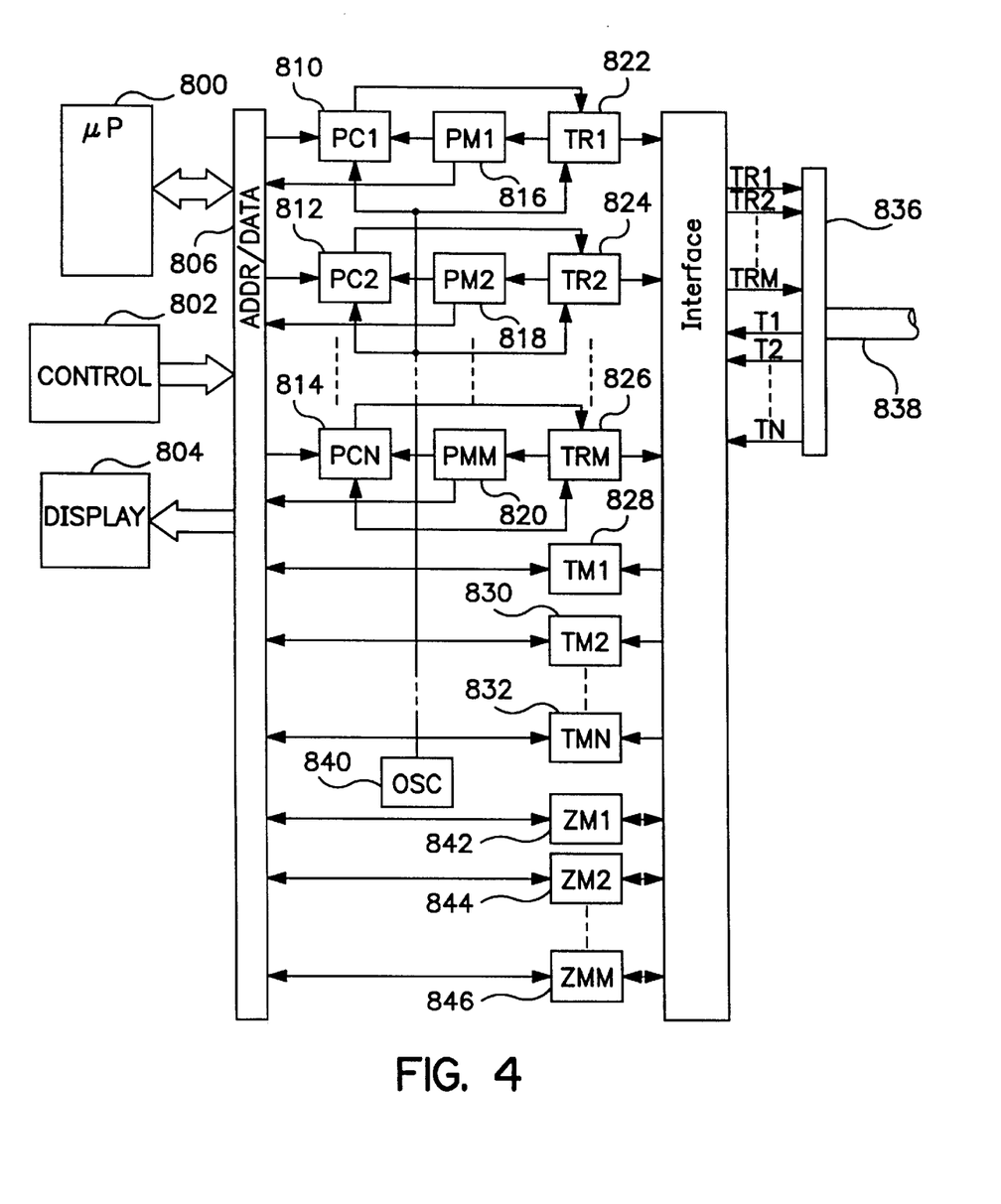
FIG. 4 is a functional block diagram of an RF generator appropriate for use in practicing the present invention, particularly adapted for use in conjunction with an ablation system employing multiple, individually activatable electrodes or multiple electrode pairs.

FIG. 4 is a functional block diagram illustrating one embodiment of an R-F generator system for use in conjunction with the present invention. In this embodiment, separately controllable R-F outputs are provided for individual ablation electrodes or electrode pairs on an associated R-F ablation device, for example as in FIG. 2B. The R-F generator could of course also be used with ablation devices having only a single electrode or electrode pair as in FIG. 2A. With the exception of the electrogram amplitude measurement circuits discussed below, the generator corresponds generally to that described in conjunction with FIG. 14 of the '961 patent issued to Maguire, et al., cited above. The RF generator disclosed in the '961 patent provides feedback control of R-F power based upon either measured power (constant power) or temperature. The present invention is somewhat easier to implement in conjunction with the constant power mode, but may also be adapted to a temperature-regulated mode or to other feedback power regulation mechanism.

Display 804 and controls 802 are connected to a digital microprocessor 800, which permits interface between the user and the remainder of the electrical components of the system. Microprocessor 800 operates under control of stored programming defining its operation including programming controlling its operation according to the present invention, as discussed in more detail below. Microprocessor 800 provides control outputs to and receives input signals from the remaining circuitry via address/data bus 806. In particular, the microprocessor 800 provides for monitoring of power, current, voltage, impedance and temperature. As necessary, the microprocessor will provide this information to the display 804. Additionally, the microprocessor 800 permits the user to select the control mode (either temperature or power) and to input the power set point, temperature set point, and a timer set point to the system. The primary source of power for the radio-frequency generator may be a 12 V battery rated at 7.2 ampere-hours. Alternatively, the device may be AC powered. A back-up battery (not shown) such as a lithium cell may also be provided to provide sufficient power to the microprocessor 260 to maintain desired memory functions when the main power is shut off.

The power supply system as illustrated includes a desired number "M" of individually controllable R-F power supplies and receives temperature inputs from a desired number "N" of temperature sensing devices in the ablation device, illustrated schematically at 838 and receives temperature inputs from a desired number "M" of impedance monitoring circuits. Each R-F power supply includes a transformer (822, 824, 826), a power control circuit (810, 812, 814) and a power measurement circuit (816, 818, 820). A crystal-locked radio-frequency oscillator 264 generates the switching pulses, which drive both the power transformers (822, 824, 826) and the power controllers (810, 812, 814). Power controllers (810, 812, 814) may be analog controllers which operate by pulse-width modulation by comparing a power set point signal from microprocessor 800 with an actual power signal generated by a power measurement circuit (816, 818, 820), which may, for example, include a torroidal transformer coupled to the power output from the associated transformer (822, 824, 826). The power measurement circuits (816, 818, 820) multiply the output current and voltage and provide the resulting actual power signal to both the power controllers (810, 812, 814) and the microprocessor 800.

The R F power output of the transformers (822, 824, 826) is provided to inter face board 808, and thereby is provided to the ablation electrode or electrodes on the ablation device 838. Separate analog comparator circuits (not illustrated) may also be provided for monitoring the output of the power measurement circuits (816, 818, 820), in order to shut-off current to the output transformers (822, 824, 826) if the power exceeds a limit, typically 55 watts. Power transformers (822, 824, 826) may include center taps, which receive the outputs of the power controllers (810, 812, 814). Secondary windings of the transformers (822, 824, 826) may provide for continuous monitoring of the applied voltage in order to permit the power calculations by power measurement circuits (816, 818, 820).

The illustrated power R-F generator system employs software controlled temperature processing, accomplished by micro processor 800, which receives the "N" temperature input signals from temperature measurement circuits (828, 830, 832), each of which are coupled to a corresponding temperature sensor in ablation device 838 by means of an electrical connector, illustrated schematically at 836 and interface circuit 834. If programmed to operate in the temperature controlled mode, processor 800 receives the "N" temperature signals and, based upon the indicated temperatures, defines power set points for each of the power control circuits (810, 812, 814), which in the manner described above control the power levels applied to electrodes on the catheter through interface 834. Processor 800 may also selectively enable or disable any of the "M" provided R-F power sup plies, in response to external control signals from controls 802 or in response to detected anomalous temperature conditions.

In addition to the circuitry as described above and disclosed in and disclosed in the Maguire, et al. '961 patent, the apparatus of FIG. 4 includes multiple impedance monitoring circuits ZM1, ZM2 . . . ZMM (842, 844 and 846 respectively), which may operate as described in U.S. Pat. No. 5,733,281, issued to Nardella, or U.S. Pat. No. 5,863,990, issued to Li, also both incorporated herein by reference in their entireties to measure an impedance between electrodes on a RF ablation device. Impedance may be measured between the ablation electrodes or between electrodes located adjacent the ablation electrodes, as described in U.S. Pat. No. 5,558,671, incorporated by reference above. Individual impedance measurements made by measurement circuits 842, 844 and 846 are provided to the address/data bus 806 and thence to microprocessor 800 for analysis to determine whether the impedance over time, indicates that the lesion associated with the measured impedance is completely transmural. As discussed in more detail below, a determination of transmurality is made in response to a detection of a series of impedance measurements that are relatively constant, over a desired period of time or over a defined number of successive impedance measurements. In some embodiments, an abrupt rise in impedance may also be employed to terminate delivery of ablation energy.

As an alternative to dedicated impedance monitoring circuits, the microprocessor may employ voltage and current measurements of impedance measurement signals generated by the power transformers (822, 824, 826) to derive impedance and may use such derived impedance values in conjunction with the present invention. For example, measurement of impedance in this fashion is disclosed in U.S. Pat. No. 5,540,681, issued to Struhl, et al, cited above or U.S. Pat. No. 5,573,533, issued to Struhl, also incorporated herein by reference in its entirety.

In cases in which an alternative ablation energy generation apparatus is employed, particularly those in which a rise in tissue temperature is induced, e.g. laser, microwave or thermal ablation, the R-F generation circuitry of FIG. 4 would be replaced with a corresponding alternative ablation energy generation apparatus. The measurement of tissue impedance and its use according to the present invention, however, may still be useful in conjunction with these alternative ablation energy generation systems.

Figure 5A:
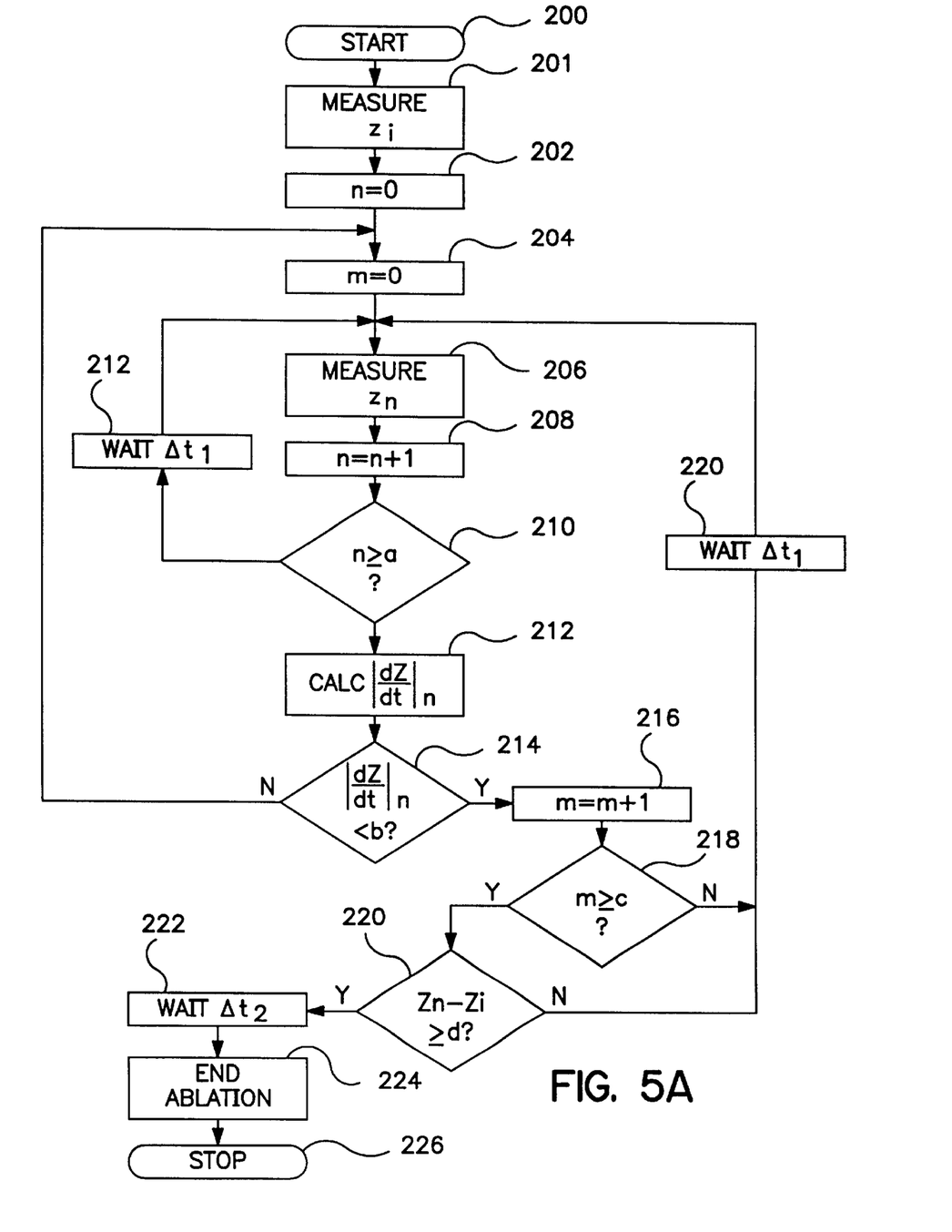
FIG. 5a is a functional flow chart illustrating a first mode of operation of the device illustrated in FIG. 4 in practicing the present invention.

FIG. 5A is a functional flow chart illustrating the operation of a device as in FIG. 4, according to the present invention. The flow chart of FIG. 5A illustrates operation of the device of FIG. 4 to control provision of R-F energy to an individual electrode or electrode pair. In the event that multiple electrodes or electrode pairs are employed, the control methodology of FIG. 5A would be applied to each electrode or electrode pair individually, as discussed in more detail below in conjunction with FIGS. 7 and 8.

The flow chart of FIG. 5A illustrates a method of assessing transmurality and terminating delivery of ablation energy to an electrode or an electrode pair responsive to detection of a plateau in impedance in conjunction with a detected drop in impedance. Following the detection of a plateau in conjunction with the required impedance drop, the device waits a defined time period and then terminates the application of ablation energy to the associated electrode pair. Measurement of impedance in tissue associated with the electrode pair may be made using the ablation electrodes themselves or electrodes located in proximity to the ablation electrodes, for example as described in the Yates '671 patent, incorporated by reference above.

After initialization at 200, the microprocessor 800 (FIG. 4) initiates delivery of ablation energy at 201 and causes the impedance measurement circuitry associated with the electrode or electrode pair being evaluated or derives impedance based on applied voltage and current as discussed above to acquire a base line or initial impedance $Z_i$, which may be, for example the maximum impedance during the first three seconds of ablation. At 202 and 204 counts "n" "m" are reset to zero. The microprocessor thereafter acquires a current impedance value $Z_n$ at 206. The value of "n" is incremented at 208 and compared with a predefined value "a" at 210 to determine whether a sufficient number of impedances have been measured in order to calculate the rate of change of impedance (dZ/dt). For example, dZ/dt may be calculated by taking the measured impedance $Z_n$ and comparing it to the preceding measured impedance $Z_{n-1}$, in which case n would have to be greater or equal to 2 in order for dZ/dt to be calculated. Alternatively, dZ/dt may be calculated by taking the measured impedance $Z_n$ and comparing it to the previously measured impedance $Z_{n-2}$, in which case n would have to be greater or equal to 3 in order for dZ/dt to be calculated. If "n" is less than "a" at 210, the microprocessor waits an impedance sampling interval $\Delta t_1$ which may be, for example, 0.2 seconds, and then triggers an impedance measurement again at 206. This process continues until there are a sufficient number of collected impedance measurements to calculate dZ/dt at 212.

At 212, the microprocessor 800 employs the stored impedance measurements to calculate dZ/dt, which may, for example, be calculated as equal to $(1/(2\Delta t_1))(Z_n - Z_{n-2})$. The absolute value of dZ/dt, i.e., $|dZ/dt|_n$ is employed to assess whether or not an impedance plateau has been reached at 214. The microprocessor checks at 214 to determine whether $|dZ/dt|_n$ is less than a defined constant b, indicative of a minimal rate of change of impedance. In the case of an elongated, fluid irrigated ablation electrode similar to that illustrated in FIG. 2A, for example using an electrode of approximately 5 centimeters in length operated in a constant power mode with a power of less than 27 watts, an appropriate value of "b" might be 1.0. For other electrode configurations and other power levels, the value of "b" would have to be adjusted. Other power control modes, e.g. temperature controlled would similarly require adjustment of this parameter. The value of "b" and other parameters employed to determine transmurality using the present invention can be determined empirically in the laboratory by applying the specific electrode set and R-F generation system in question to test specimens, reading impedances at defined sample intervals and using the results to optimize the various parameters.

In the event that $|dZ/dt|_n$ is sufficiently small in value at 214, the count "m" is incremented at 216 and m is compared to a third constant "c" which sets forth the defined number of low value $|dZ/dt|_n$ measurements required to detect an impedance plateau. For example, in a system as described herein, "c" may be 6–12. Alternatively, rather than requiring an entire series of measured $|dZ/dt|_n$ values to be less than "b", a requirement that a defined proportion of the $|dZ/dt|_n$ values must be less than "b" may be substituted, e.g. 8 of 12, or the like.

If the number of low values of $|dZ/dt|_n$ is less than "c" at 218, the microprocessor waits the impedance sampling interval $\Delta t_1$ at 220 and continues to acquire successive impedance measurements until sufficient number of sequential low values of $|dZ/dt|_n$ have occurred at 218. At that point, the microprocessor then compares the current impedance value $Z_n$ with the initial impedance value $Z_i$ to determine whether a sufficient impedance drop has occurred. If not, the microprocessor waits for the next impedance sampling interval at 220 and continues to collect impedance measurements and make calculations of $|dZ/dt|_n$ until such time as an impedance plateau is recognized at 218 and a sufficient impedance drop is recognized at 220. When both of these criteria have been met at 220, the microprocessor than waits for an additional time interval $\Delta_{t2}$ to assure completeness of the lesion at 222 and thereafter terminates the provision of ablation energy to the specific electrode pair being regulated at 224 and the ablation process with regard to that electrode or electrode pair is terminated at 226.

Figure 5B:
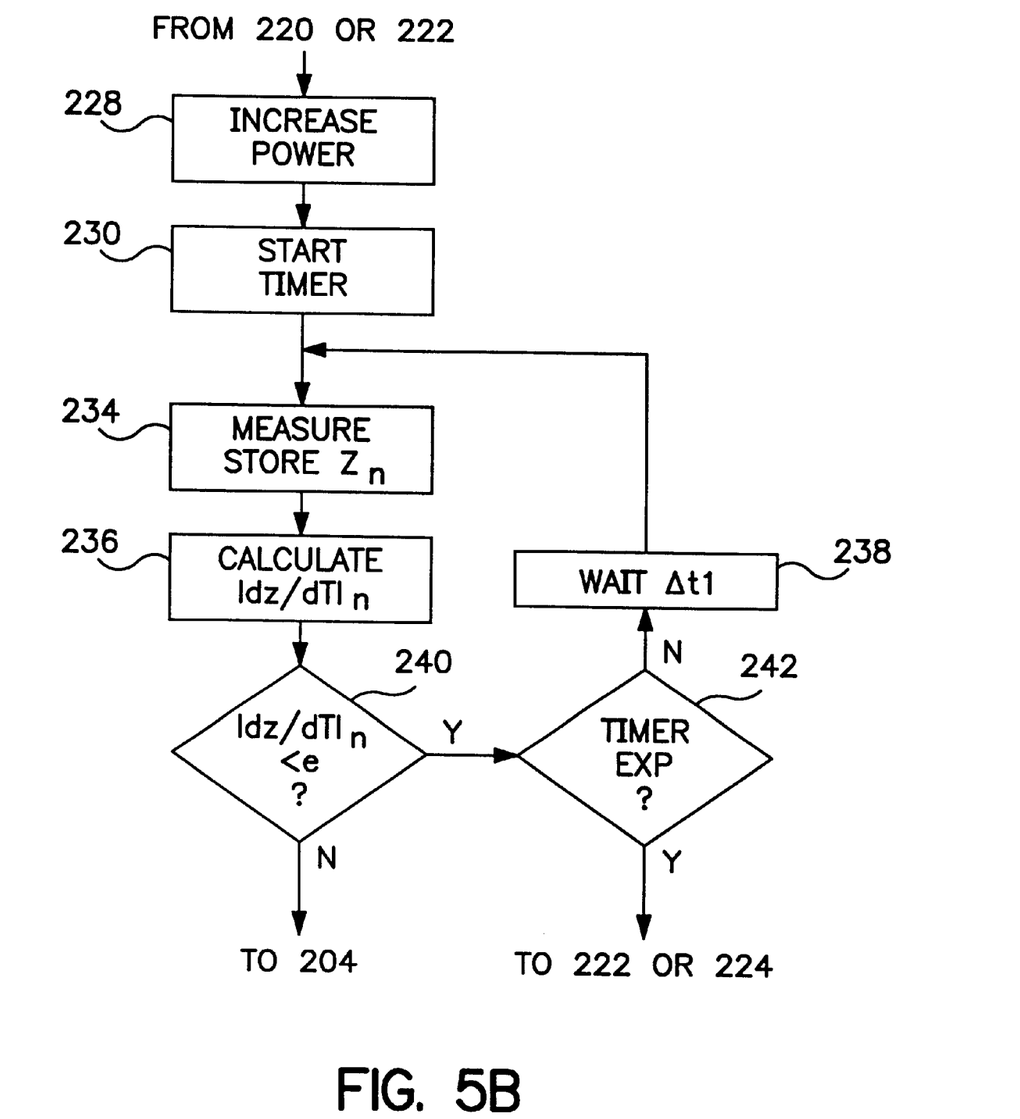
FIG. 5b illustrates an alternative mode of operation of a device as in FIG. 4 in practicing the present invention.

FIG. 5B illustrates an additional set of operations for implementing a transmurality measurement method generally as in FIG. 5A. The operations of FIG. 5B may either be a substituted for step 222 of FIG. 5A or alternatively may be performed before or after step 222. In the additional operations illustrated in FIG. 5B, the microprocessor increases the power to the electrodes under consideration slightly at 228 and sets a timer at 230. The microprocessor then causes the impedance measurement apparatus associated with the electrodes under consideration to measure current impedance at 234 and calculate $|dZ/dt|_n$ at 236, in the same fashion as discussed above. In the event that the value of $|dZ/dt|_n$ is greater then a defined constant "e" at 240, the microprocessor returns to 204 and resets the value of "m" to zero, essentially reinitializing the search for an impedance plateau. The value of "e" may be equal to "b" or may be different. If the value of $|dZ/dt|_n$ is sufficiently small at 240, the microprocessor checks at 242 to determine whether the timer has expired. If not, the microprocessor waits the impedance sampling interval $\Delta_{t1}$ at 238 and continues to collect impedance values and calculate $|dZ/dt|_n$ values until expiration of the timer at 242, at which point it either terminates ablation at 224 or initiates the waiting period $\Delta_{t1}$ at 222.

Figure 6:
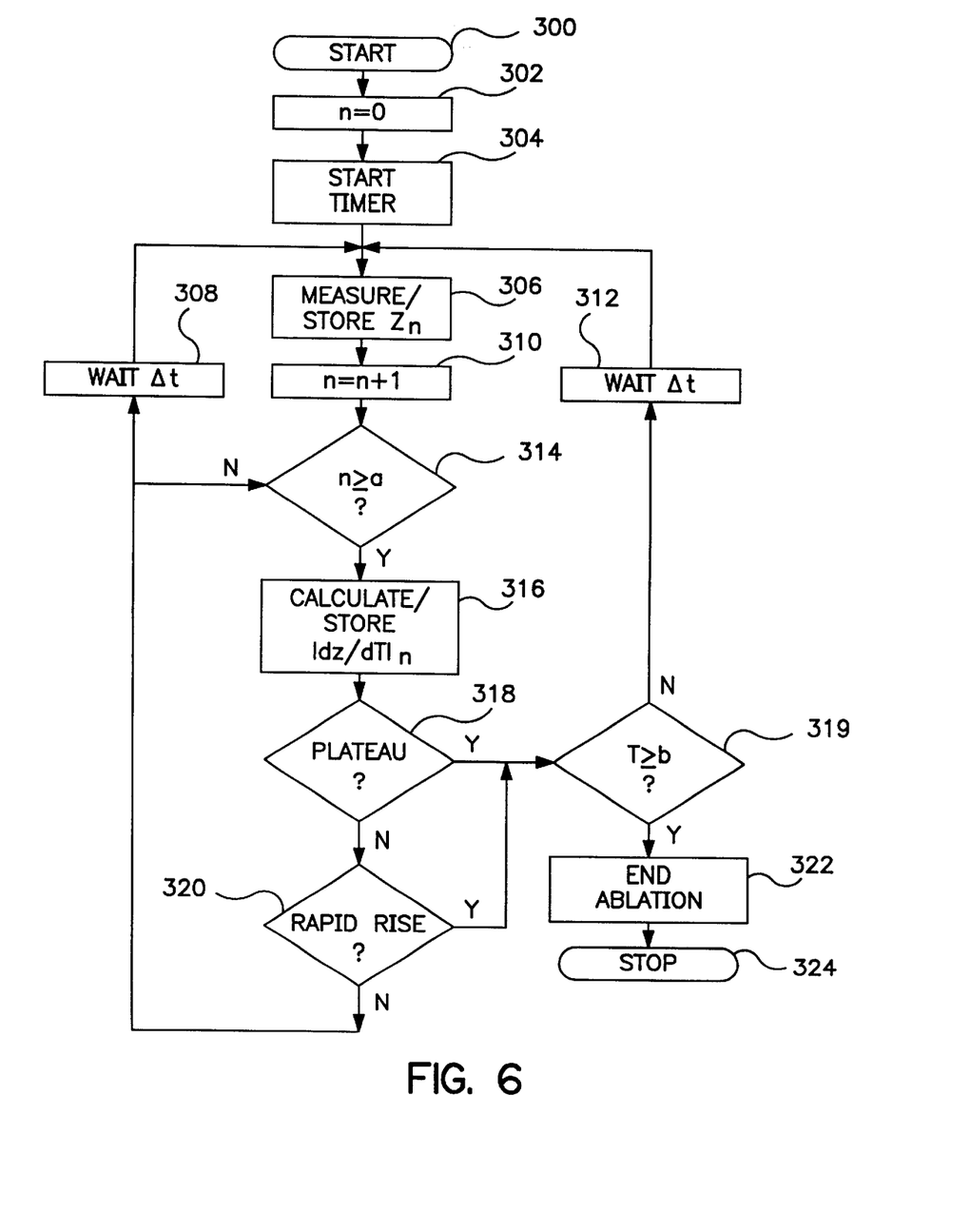
FIG. 6 illustrates an additional alternative mode of operation of a device as in FIG. 4 in practicing the present invention.

FIG. 6 illustrates a second basic approach to assessment of transmurality and control of delivery of ablation energy to an electrode pair. In the same fashion as for FIGS. 5a and 5b, the procedure defined by the flow chart of FIG. 6 it should be understood to be employed in conjunction with an impedance measurement circuit with a single electrode pair, which procedure would be repeated for other electrodes or electrode pairs, if present. After initiation at 300, the value of "n" is set to Zero at 302 and a timer is initiated at 304, used to determine that a sufficient amount of time has passed prior to termination of ablation. For example, in the context of a bipolar irrigated hemostat similar to FIG. 1 and 2a as described above, having electrode lengths of 2 to 5 centimeters and receiving RF energy at a level of 27 watts or less, ten seconds may be an appropriate time interval for the timer initiated at 304.

The microprocessor than measures the current impedance $Z_n$ at 310 increments the value of "n" at 310 and checks at 314 to determine whether an adequate number of impedance measurements have been accumulated to make a calculation of dZ/dt at 314, in the same fashion as discussed above in conjunction with FIGS. 5a and 5b. If an inadequate number of samples have been collected, the microprocessor waits the impedance sampling interval $\Delta_t$ at 308 and continues to collect impedance measurements until an adequate number "a" of measurement have been collected. In the specific example presented, "a" may be set equal to 19 and $\Delta_t$ may be 0.2 seconds. After an adequate number of impedance measurements have been collected at 314, the microprocessor calculates the value of $dZ/dt_n$ and $|dZ/dt|_n$ at 316. In conjunction with the specific mechanism of plateau detection illustrated in FIG. 6, filtered or average impedance values $Z_a$ may be employed to calculate dZ/dt and $|dZ/dt|_n$.

For example, at 316, the microprocessor may calculate the value of dZ/dt according to the following method. The microprocessor may employ a 5 point moving average filter to produce an average impedance value $Z_a$, which is equal to $(Z_n+Z_{n-1}+Z_{n-2}+Z_{n-3}+Z_{n-4})/5$. The value of $dZ/dt_n$ and $|dZ/dt|_n$ may be same fashion as in conjunction with the flow charts of FIG. 5A and 5B discussed above, substituting the averaged impedance values $Z_a$ for the individual impedance values $Z_n$ as employed in the previous flow charts. In this case, $dZ/dt_n$ would be $(1/(2\Delta_t))(Z_n-Z_{n-2})$ and $|dZ/dt|_n$ would be the absolute value of dZ/dt.

At 318, microprocessor 308 may attempt to determine whether an impedance plateau has been reached employing the following method. The microprocessor reviews the preceding 15 measurements of $dZ/dt_n$ and $|dZ/dt|_n$ and applies three criteria to those values, all three of which must be met in order for an impedance plateau to be detected. For a fluid irrigated hemostat as described, the rules may be as follows: for n=1 to 15; $|dZ/dt|_n$ must be less than or equal to 1 for all 15; and for n=1 to 15 the value of $dZ/dt_n$ must be less than or equal to 0.75, for thirteen of the 15; and for n=1 to 15, $|dZ/dt|_n$ must be less than or equal to 0.5, for 10 of the 15. If all of these criteria are met at 318, the microprocessor checks at 319 to determine whether an adequate period of time has elapsed since ablation was initiated, if not, the microprocessor waits for the impedance sampling interval $\Delta_t$ at 312 and continues to measure impedances and calculate values of dZ/dt according to the above described method until both a plateau is present and the defined time period "b" has elapsed at 319. After the required time period at "b" at 319 has elapsed, delivery of ablation energy to the associated electrode or electrode pair is terminated at 322 and the ablation process ceases at 324 as to that electrode pair.

In this embodiment, in the event that an impedance plateau fails to manifest itself, the microprocessor may nonetheless safely terminate provision of ablation energy to the electrode pair under consideration in response to a detected rapid rise in impedance, which normally follows the impedance plateau. In the event that a plateau is not detected at 318, the microprocessor checks the preceding stored values of $dZ/dt_n$ to look for a rapid rise in impedance. For example, a rapid rise in impedance may be detected using the following rule: for n=1 to 10, $dZ/dt_n$ must be greater than or equal to 1.0 for all 10. If this rapid rise criteria is met at 320, the processor checks to see whether the required minimal time period has elapsed at 319, and if so, terminates ablation at 322 as discussed above. If the minimal time interval "b" has not elapsed, the microprocessor continues to acquire measurements of impedance and continues to calculate values of dZ/dt and $|dZ/dt|_n$ until either an impedance plateau is detected at 318 or a rapid rise in impedance is detected at 320 and the minimum time interval has expired at 319.

Figure 7:
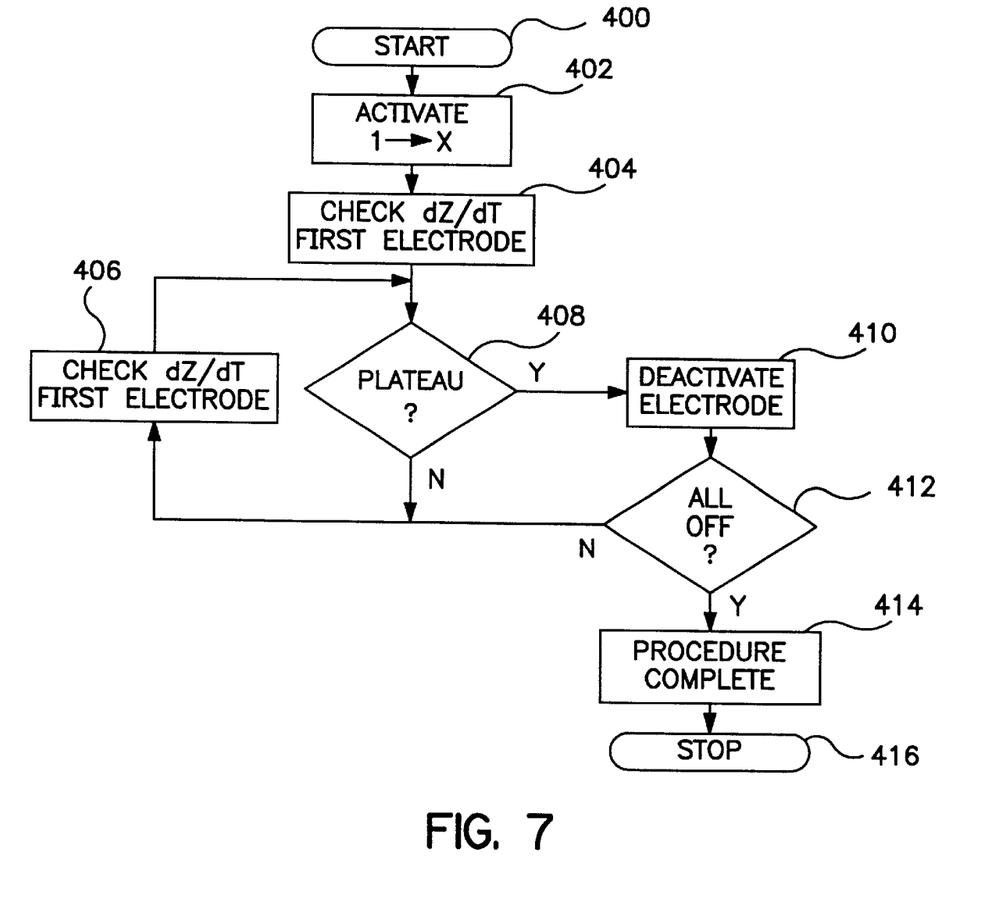
FIG. 7 illustrates a first mode of operation of a device as in FIG. 4 to activate and deactivate of individual electrodes or electrode pairs.

FIG. 7 is a function flow chart illustrating the over-all operation of the device in conjunction with a multi electrode or multi electrode pair ablation apparatus. In the flow chart of FIG. 7, all the electrodes are activated simultaneously and individual electrodes or electrode pairs are deactivated in response to impedance measurements associated with the electrode pair indicating that the lesion formed between that electrode pair is completely transmural. In this circumstance, the ablation system works as follows.

After initialization at 406, all electrodes 1–x are activated at 402, meaning that ablation energy is provided to all electrodes and electrode pairs. The microprocessor then checks the value of dZ/dt and/or $|dZ/dt|$ at the first of the electrode pairs at 404, using any of the mechanisms discussed above in conjunction with FIGS. 5a, 5b and 6. At 408, the microprocessor checks using any of the mechanisms described above to determine whether an impedance plateau has been reached or, in the event that additional criteria for shut off of ablation energy are provided, to see whether any of these additional criteria are reached. If so, the electrode being examined is deactivated at 410 by ceasing the delivery of ablation energy to the electrode or electrode pair. If not, the microprocessor checks the value of dZ/dt and/or $|dZ/dt|$ for the next electrode at 406. This process continues until all electrodes are deactivated at 412, after which the procedure is deemed complete at 414 and the ablation process is terminated at 416.

Figure 8:
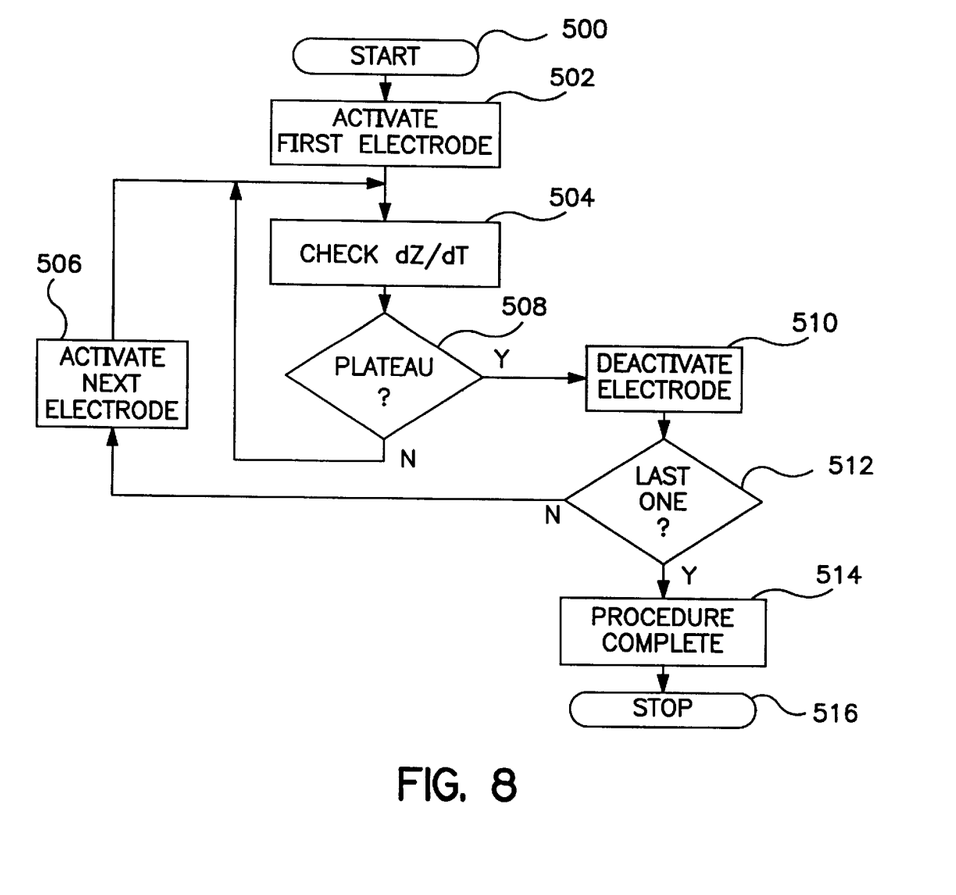
FIG. 8 illustrates a second mode of operation of a device as in FIG. 4 to activate and deactivate individual electrodes or electrode pairs.

FIG. 8 illustrates a functional flow chart of overall operation of a device in which a multi-electrode or multi-electrode pair ablation apparatus is employed, as in FIG. 7. In this embodiment, however, electrodes or electrode pairs are activated initially and sequentially. After initialization at 500, the microprocessor activates delivery of ablation energy to the first electrode at 502, checks dZ/dt and/or $|dZ/dt|$ at 504 and, in the same manner as described for FIG. 7 above, checks to determine whether the impedance plateau criteria and/or other criteria as described above have been met. If so, the electrode is deactivated at 510. If not, application of ablation energy continues until the plateau criterion or other criteria are met as described above. After deactivation of an electrode at 510, the microprocessor checks to determine whether all electrodes have been activated and deactivated at 512, if not, the microprocessor then activates the next electrode at 506 and initiates delivery of ablation energy to that electrode. This process continues until the last electrode has been deactivated at 512, following which the microprocessor determines that the ablation process is complete at 514 and the ablation process is stopped at 516.

The overall operational methodology of FIG. 7 is believed to be desirable in that it allows for a more rapid completion of an ablation procedure. However, the overall operational method is described in FIG. 8 has the advantage that it may allow the use of a somewhat simplified generator because that multiple, separate impedance measurement circuits, power control circuits, and the like need not be provided for each electrode or electrode pair. A simple switching mechanism may be used in conjunction with only a single RF generator and impedance measurement circuit to successively apply energy to each electrode and to monitor impedance according to the invention.

In conjunction with the above specification, we claim:

1. A method of ablation, comprising;

applying ablation energy to a first tissue site;

monitoring impedance of the first tissue site; and responsive to occurrence of an impedance plateau at the first tissue site, the impedance plateau determined by a plurality of $|dZ/dt|$ values In a series of monitored $|dZ/dt|$ values being below a preselected value, terminating application of ablating energy to the first tissue site.

2. A method as in claim 1 wherein the applying of ablation energy to the first tissue site comprises applying R-F energy using a first R-F electrode.

3. A method as In claim 2 wherein the monitoring of impedance of the first tissue site comprises monitoring impedance using the first R-F electrode.

4. A method as in claim 1 wherein the applying of R-F energy to the first tissue site comprises applying R-F energy using an irrigated first R-F electrode.

5. A method as in any of claims 1–4, wherein the terminating of application of ablating energy to the first tissue site comprises terminating application of ablation energy responsive to a series of monitored impedances that have an acceptable degree of change.

6. A method as in any of claims 1–4, wherein the terminating of application of ablating energy to the first tissue site comprises terminating application of ablation energy responsive to a series of monitored impedances that have an acceptable rate of change.

7. A method as in claim 1, further comprising:

applying ablation energy to a second tissue site;

monitoring impedance of the second tissue site; and responsive to occurrence of an impedance plateau at the second tissue site, terminating application of ablating energy to the second tissue site.

8. A method as in claim 7, wherein the applying of ablation energy to the second tissue site comprises applying R-F energy using a second R-F electrode.

9. A method as in claim 8, wherein the monitoring of impedance of the second tissue site comprises monitoring impedance using the second R-F electrode.

10. A method as in claim 7, wherein the applying of R-F energy to the second tissue site comprises applying R-F energy using an irrigated second R-F electrode.

11. A method as in any of claim 7–10, wherein the terminating of application of ablating energy to the second tissue site comprises terminating application of ablation energy responsive to a series of monitored impedance that have an acceptable degree of change.

12. A method as in any of claims 7–10, wherein the terminating of application of ablating energy to the second tissue site comprises terminating application of ablation energy responsive to a series of monitored impedances that have an acceptable rate of change.

13. A method as in any of claims 7–10, wherein the applying of ablation energy to the first and second tissue sites is initiated simultaneously.

14. A method as in any of claims 7–10, wherein the applying of ablation energy to the second tissue site is initiated following termination of application of ablation energy to the first tissue site.

* * * * *